United States Patent
Pasquet et al.

(10) Patent No.: US 6,716,245 B2
(45) Date of Patent: Apr. 6, 2004

(54) INTERSOMATIC IMPLANT

(75) Inventors: Denis Pasquet, Pessac (FR); Régis Le Couedic, Bordeaux (FR)

(73) Assignee: Spine Next, Bordeaux (FR)

( * ) Notice: Subject to any disclaimer, the term of this patent is extended or adjusted under 35 U.S.C. 154(b) by 0 days.

(21) Appl. No.: 10/312,033

(22) PCT Filed: Jul. 6, 2001

(86) PCT No.: PCT/FR01/02178

§ 371 (c)(1),
(2), (4) Date: Dec. 19, 2002

(87) PCT Pub. No.: WO02/03895

PCT Pub. Date: Jan. 17, 2002

(65) Prior Publication Data

US 2003/0109928 A1 Jun. 12, 2003

(30) Foreign Application Priority Data

Jul. 12, 2000 (FR) .............................................. 00 09091

(51) Int. Cl.⁷ ................................ A61F 2/44; A61F 2/46
(52) U.S. Cl. ...................................... 623/17.11; 606/99
(58) Field of Search .......................... 623/17.11, 17.15, 623/17.16, 23.5; 606/61, 86, 99

(56) References Cited

U.S. PATENT DOCUMENTS

| | | | | |
|---|---|---|---|---|
| 4,892,545 A | * | 1/1990 | Day et al. ..................... | 623/17 |
| 5,192,327 A | | 3/1993 | Brantigan | |
| 5,658,336 A | * | 8/1997 | Pisharodi ..................... | 623/17 |
| 5,735,857 A | * | 4/1998 | Lane ............................ | 606/99 |
| 5,968,051 A | * | 10/1999 | Luckman et al. ............. | 606/88 |
| 6,015,937 A | * | 1/2000 | Branemark ................... | 623/16 |
| 6,143,033 A | * | 11/2000 | Paul et al. ................. | 623/17.11 |
| 6,159,211 A | * | 12/2000 | Boriani et al. ................ | 606/61 |
| 6,383,221 B1 | * | 5/2002 | Scarborough et al. ... | 623/17.11 |
| 6,432,106 B1 | * | 8/2002 | Fraser ......................... | 606/61 |
| 6,558,423 B1 | * | 5/2003 | Michelson ............... | 623/17.11 |

FOREIGN PATENT DOCUMENTS

| | | |
|---|---|---|
| FR | 2 703 580 | 10/1994 |
| FR | 2 742 653 | 6/1997 |
| WO | WO 99/66867 | 12/1999 |

\* cited by examiner

*Primary Examiner*—Eduardo C. Robert
*Assistant Examiner*—David C Comstock
(74) *Attorney, Agent, or Firm*—Merchant & Gould P.C.

(57) ABSTRACT

The invention provides an intersomatic implant suitable for containing at least one bone graft and for being inserted in the intervertebral space along a predetermined direction. It comprises: a first portion (10) of generally annular shape surrounding an aperture (11) and presenting a top first edge (12) and a bottom first edge (14); and a second portion (16) of elongate shape along its main axis (A) presenting a bottom second edge (18) and a top second edge (20), and interconnecting two facing opposite regions of said first portion (10) along said predetermined direction, thereby dividing said aperture (11) into two housings suitable for containing said bone graft, at least one of said bottom and top second edges projecting from the space defined by said bottom and top first edges (14, 12) of the first portion (10).

18 Claims, 4 Drawing Sheets

INTERSOMATIC IMPLANT

The present invention relates to an intersomatic implant intended in particular for holding a bone graft stationary between two vertebrae, and more particularly to a cage suitable for containing grafts.

The fields of application of the invention lie in particular in surgical treatment of degenerative disks.

In general, such treatment involves an operation seeking to lock two adjacent vertebrae together, with this being done by interposing bone grafts between them so that once the graft has taken the vertebrae are bonded together. However, given the mechanical stresses exerted on the grafts by the two vertebrae, there is a danger of the grafts being expelled or crushed.

To mitigate that drawback, it is known to hold the grafts in place by means of cages whose top and bottom ends bear against the vertebrae via edges around openings that enable the grafts to make contact with the superior and inferior vertebral plates.

Locking two vertebrae together by means of an element of bone presents the advantage of imparting uniform mechanical properties to the resulting assembly, and in particular uniform elastic deformation of said assembly as characterized by its modulus of elasticity.

Unfortunately, the cages in general use are made of titanium alloy and the modulus of elasticity of such alloys are at least ten times greater than the modulus of elasticity of vertebral bone. Thus, intersomatic cages that remain permanently between vertebrae, themselves give rise to discontinuity in the mechanical properties of the assembly made up of two bonded-together vertebrae.

In order to conserve uniform elastic deformation, proposals have been made to use cages made of macromolecular materials having moduli of elasticity that are of the same order of magnitude as those of bone. However, plastics material cages which are generally annular in shape are not as strong as titanium alloy cages and inserting them by force between vertebrae can lead to their edges rupturing. The solution which consists in enlarging their edges reduces the volume available for grafts and thus the bonding force between two vertebrae. Furthermore, since they are not as hard as titanium alloy cages, their edges penetrate to a smaller extent into the vertebral plates, so they are not prevented so effectively from moving relative to the vertebrae.

An object of the present invention is to provide an intersomatic implant made of macromolecular materials, the implant being of the cage type, presenting top and bottom openings of the same order of magnitude as the openings in titanium alloy cages so as to retain a graft area of substantially equal size and thus ensure that the graft is held in a fixed position relative to the vertebrae.

To this end, the present invention provides an intersomatic implant suitable for containing at least one bone graft and for being inserted in the intervertebral space along a predetermined direction, the implant comprising: a first portion of generally annular shape surrounding an aperture and presenting a top first edge and a bottom first edge; and a second portion of elongate shape along its main axis presenting a bottom second edge and a top second edge, and interconnecting two facing opposite regions of said first portion along said predetermined direction, thereby dividing said aperture into two housings suitable for containing said bone graft, at least one of said bottom and top second edges projecting from the space defined by said bottom and top first edges of the first portion.

Thus, a characteristic of the intersomatic implant lies in said generally annular first portion being reinforced by an elongate second portion situated in the determined direction along which said implant is pushed in between the vertebrae. As a result, in spite of the stresses that are exerted on the first portion while it is being impacted between the vertebrae, which stresses tend to deform the first portion in its midplane so as to move the two substantially opposite regions towards each other, said first portion retains its generally annular shape. In addition, the top and bottom open areas, subdivided into two by said second portion, are of the same order of magnitude as the areas of a titanium alloy intersomatic implant, thus making it possible to obtain a graft area that is substantially identical.

In addition, the bottom and top second edges project out from the space defined by said bottom and top first edges of the first portion, such that not only is the implant held between the vertebrae by contact between the edges of said first portion against the vertebral plates, but it is also held by said elongate second portion which bears against the vertebral plates which are of biconcave shape.

The implant of the invention is prevented from moving between the vertebrae in a manner that is more reliable than with a conventional implant that is of annular structure, only.

In a first embodiment of the invention, said first portion and said second portion are connected together so as to form a single piece, ensuring that they are entirely cohesive.

Advantageously, said bottom and top second edges of said second portion are curvilinear in shape with their ends running into said bottom and top first edges respectively of said first portion. As a result, the shape of the second portion coincides substantially with the shape of the available space situated between the vertebrae.

In a preferred embodiment of the invention, said first portion is pierced laterally along said main axis of said second portion so as to provide a blind hole extending in said second portion, said blind hole being suitable for receiving an insertion tool.

As explained below in greater detail, in this preferred embodiment, the implant is inserted between two adjacent vertebrae by force and it is necessary to have complete control over the insertion direction. In order to conserve a constant angle of impact, the tool which pushes said implant is itself inserted into a blind hole which extends in the second portion. Thus, the end of the tool pressed against the implant is held captive in said implant during impacting and does not run any risk of puncturing tissue situated in the vicinity of the operation.

Advantageously, said bottom and top edges of said first and second portions present serrations suitable for constituting anchoring points in said vertebrae.

Thus, the sharp portions of the serrations penetrate into the walls of the vertebral plates. As a result, the implant is held between the vertebrae without any possibility of moving laterally, thus encouraging the grafts to take.

Preferably, said first portion of generally annular shape has at least one axis of symmetry and advantageously, said second portion interconnects said two opposite regions of said portion along said axis of symmetry.

This configuration makes it possible to match the implant accurately to the shape of the vertebrae, and in particular of the vertebral bodies. Since said second portion lies on the axis of symmetry, the stresses exerted on the implant during impacting are distributed uniformly.

In another preferred embodiment of the invention, said second portion interconnects said two opposite regions of said first portion along a direction that is at an angle lying in the range 0° to 90° with said axis of symmetry.

Thus, the implant can be inserted between the vertebrae more easily when the insertion is performed does not make it possible to operate symmetrically about the spinal column. It is always necessary to push the implant in along the axis of said second portion in order to avoid breaking said first portion, and at certain levels, the vertebrae are accessible laterally only. Under such circumstances, said second portion is disposed obliquely relative to the axis of symmetry of said implant.

Preferably, said first portion is generally substantially semicircular in shape.

In another preferred embodiment of the invention, said part is molded out of a macromolecular material. Thus, it can be made under economically advantageous conditions. Said part is preferably made of polyether ether ketone which is easy to mold and which presents elastic properties close to those of bone.

In a second embodiment of the invention, said second portion further comprises anchoring means projecting from said top and bottom second edges, respectively. Thus, said anchoring means are caused to penetrate by force into the surfaces of the vertebral plates while the implant is being inserted between the vertebrae, thereby ensuring that said implant is completely prevented from moving in translation relative to the vertebrae and cannot slide relative thereto.

In a particular embodiment, said anchoring means are constituted by an anchoring piece having two ends, and said second portion has a slot opening out into said bottom and top second edges so that said anchoring piece when inserted in said slot passes through said second portion, the first end projecting from said top second edge and the second end projecting from said bottom second edge of said second portion.

As a result, the anchoring piece can be inserted in the second portion at the time it is inserted between the vertebrae, should that be absolutely necessary. In addition, since the anchoring means are made as a single piece, their rigidity is increased and they do not deform during insertion.

Advantageously, said anchoring piece is substantially trapezoidal in shape, its two ends being defined by the two non-consecutive and non-parallel sides thereof. Preferably, it has a midplane, and it is inserted in said second portion so that said main axis A of said second portion intersects the two bases of the trapezoid, and its midplane is substantially perpendicular to the midplane of said first portion. Thus, by means of the aperture which is substantially in the form of a rectangular parallelepiped, the walls of the anchoring piece coincide with the walls of the aperture.

Preferably, one of the bases of the trapezoid forms two acute angles with the two non-parallel sides, and said anchoring piece is inserted in said second portion so that the insertion direction of said implant extends from the longer base towards the shorter base of the trapezoid. As a result, the anchoring piece presents a projecting point at each end, defined by the acute angle and suitable for penetrating more deeply into the vertebral body so as to be secured even more firmly thereto. In addition, the anchoring piece forms an arrow portion when it is engaged between the vertebrae, when the implant is pushed in from the larger base of the trapezoid towards the smaller base. As a result, it is impossible for the anchor piece to move in the opposite direction due to the projecting point penetrating into the vertebral plates. Preferably, the anchoring piece is made of titanium alloy, and as a result its rigidity enables better anchoring to be obtained.

The present invention also provides an intersomatic implant press for inserting an anchoring piece in the aperture of said second portion. The press of the invention comprises: a first jaw suitable for receiving said first portion in which said second portion interconnects two opposite edges, said first jaw having a central aperture in register with said slot in said second portion; and a second jaw placed facing said central slot; and said jaws are capable of being moved towards each other in such a manner that said second jaw can bear against said anchoring piece to force it into said slot or to extract it from said slot.

Other features and advantages of the invention will appear on reading the following description of particular embodiments of the invention given by way of non-limiting indication with reference to the accompanying drawings, in which:

FIG. 1 shows an intersomatic implant inserted between two adjacent vertebrae. Reference is made to FIG. 2 in order to describe an implant constituting a first embodiment of the invention that is preferably inserted between lumbar vertebrae.

Figure 1:
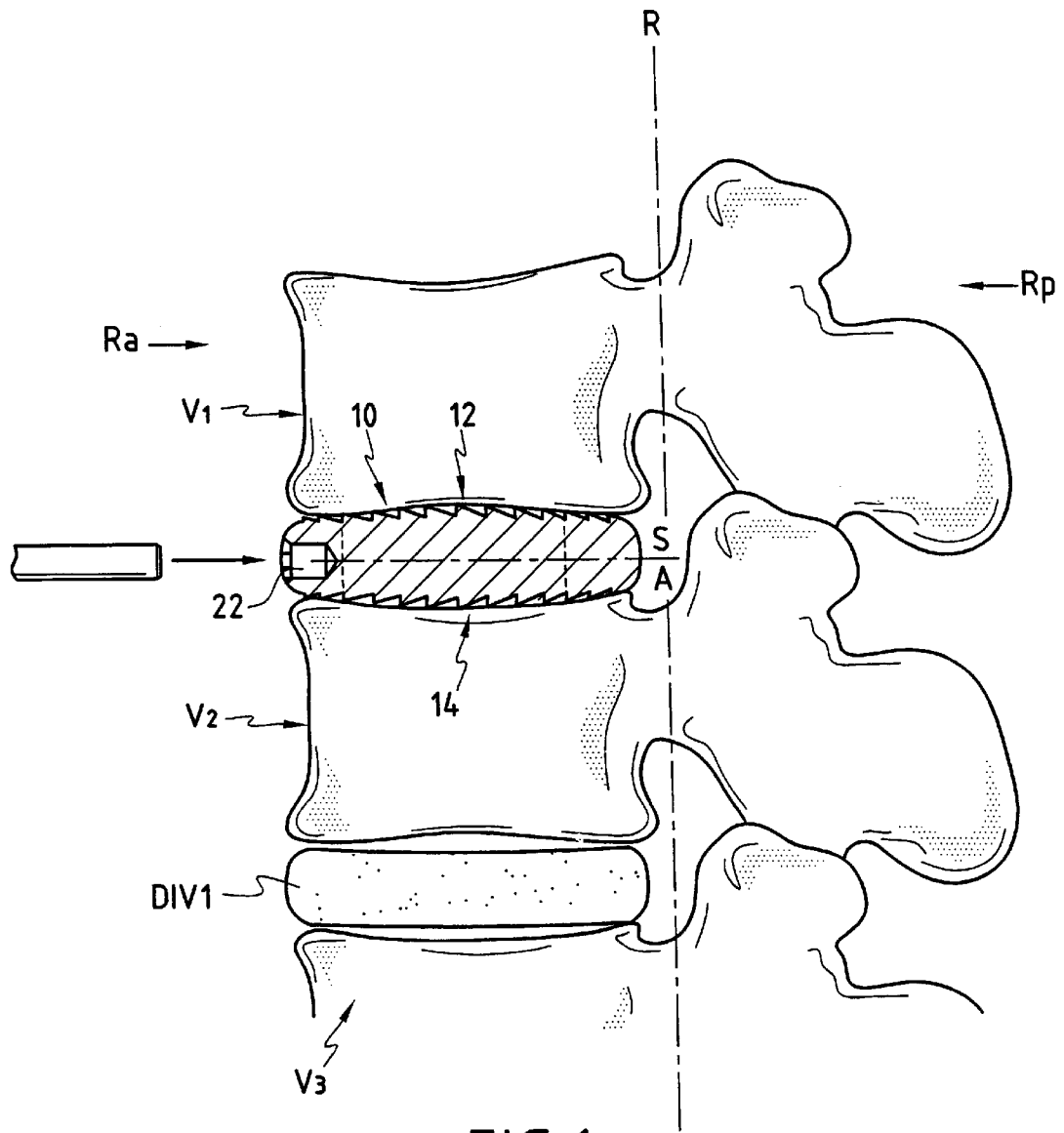
FIG. 1 is a diagrammatic fragmentary side view showing the position of the intersomatic implant of the invention between two adjacent vertebrae.

The intersomatic implant presents a first portion 10 which can be seen in profile in FIG. 1. The anterior edge Ra of the spine faces the front wall of the body and the posterior edge Rp of the spine faces the rear wall of the body.

The intersomatic implant is intended to hold bone grafts against motion between two vertebrae for the purpose of replacing an intervertebral disk. In FIG. 1, intervertebral disk DIV1 is shown as being intact between vertebrae V2 and V3.

The vertebral canal extends along the spine on the axis R and contains the spinal cord, and it will be understood that because of the vulnerability of the spinal cord, that it is preferable to insert an implant between two vertebrae using an anterior approach. This is normally the case in most operations for cervical disk hernias.

Figure 2:
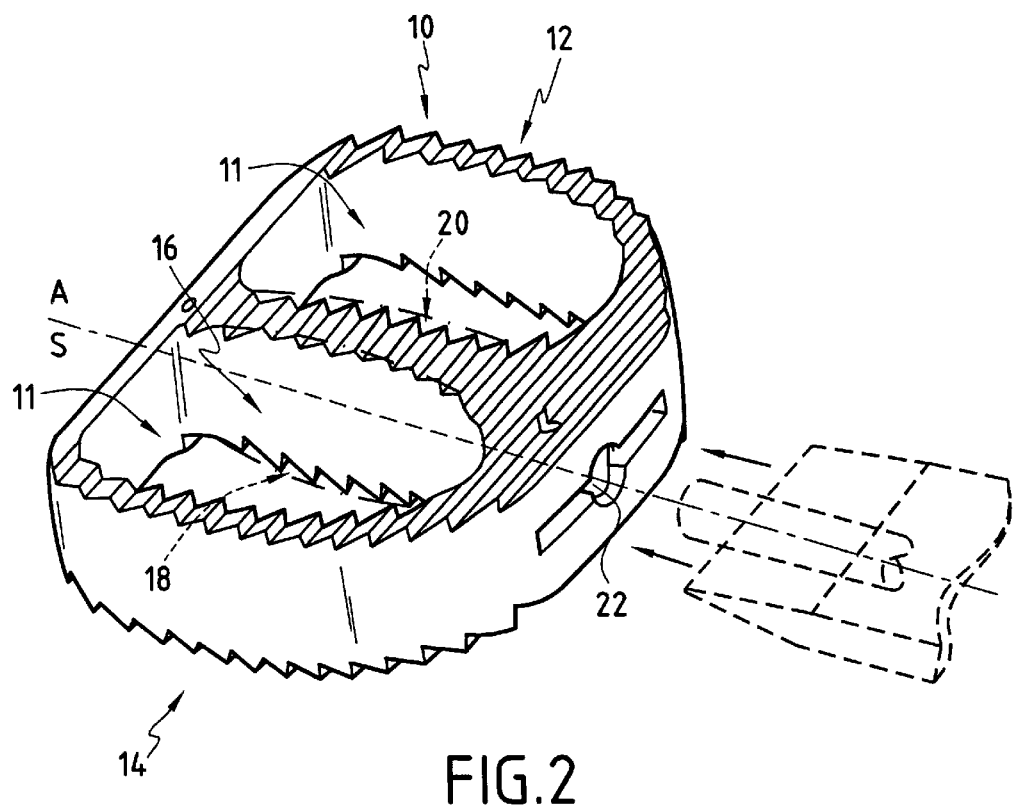
FIG. 2 is a diagrammatic perspective view showing a first embodiment of an intersomatic implant and showing a portion of the insertion tool for pressing against the implant.

In FIG. 2, where the intervertebral implant is shown in profile, there can be seen the first portion 10 which is of generally annular shape defining an aperture 11 that is divided in two by a second portion 16 that is elongate in shape along an axis A, said second portion 16 interconnecting two facing regions of the first portion 10. The top first edge 12 of the first portion 10 is situated substantially in a plane parallel to the plane defined by the bottom first edge 14 of the first portion 10. When the implant is inserted between the vertebrae, each of these first edges 12, 14 is in contact with the corresponding vertebral plate.

The apertures 11 are intended to receive bone grafts whose top portions come into contact with the bottom vertebral plate of the upper vertebra and whose bottom portions come into contact with the top vertebral plate of the lower vertebra. Thus, the grafts are contained and prevented from moving between the vertebrae in such a manner as to enable the grafts to take and provide a cohesive assembly. In general, the grafts are cortical grafts taken from the anterior iliac crest whose thickness corresponds substantially to the intersomatic space. Naturally, once bone bonding is established between the vertebrae, intervertebral implants remain permanently in place and form an integral portion of the bond.

In order to ensure that the implant is as stable as possible after it has been inserted between the vertebrae, the second portion 16 which interconnects the two opposite edges of the first portion 10 presents bottom and top second edges 18 and 20 of curvilinear shape projecting proud of the first portion 10. This shape complies with the biconcave shape of the intersomatic space and serves to establish additional bearing points for the implant against the central portions of the vertebral plates.

Prior to inserting the implant fitted with its bone grafts, the damaged intervertebral disk is extracted so as to enable the implant to be pushed in. Thereafter the implant is pushed into the intervertebral space along a predetermined direction.

This predetermined direction depends on the level of the vertebrae where the operation is performed and on the therapeutic indication.

The intersomatic implant as shown in FIG. 2 is for insertion via the anterior edge of the spine. It has a blind hole 22 pierced in the wall of the first portion 10 that is of annular shape and extending into the second portion 16 along its main axis A, which axis coincides with the axis of symmetry S of the first portion 10. The end of the insertion tool is inserted into the blind hole 22 and bears against said reinforcing second portion 16 so as to hold and guide the implant while it is being pushed into the intersomatic space.

A characteristic of the invention lies in the elongate second portion 16 being included in the first portion so as to enable the first portion to withstand the stresses that are applied thereto during impaction. For optimum ability of the implant to withstand deformation, the impacts must be applied on the axis A of the second portion 16. The blind hole 22 maintains the impacting tool at a constant direction relative to the implant, on the axis A thereof. Furthermore, the fact that the end of the insertion tool is secured to some extent to the implant makes it possible to control the path followed by the implant between the vertebral bodies.

The extent to which the implant becomes locked between the vertebrae is a function of the friction forces acting on the interfaces between the vertebral plates and edges 12, 14, 18, and 20 of the first and second portions 10 and 16. In order to increase these friction forces, the edges 12, 14, 18, and 20 are serrated so as to form anchoring points for engaging in the vertebral plates.

In a particular embodiment, the serrations slope in the direction opposite to the insertion direction such that in the insertion direction the friction forces between the implant and the vertebrae are less than the friction forces which appear in the opposite direction. This locks the implant against moving in the direction opposite to its insertion direction.

The annular first portion 10 shown in FIG. 2 has an axis of symmetry S which coincides with the longitudinal axis of symmetry of the second portion 16, thus enabling insertion to be performed perpendicularly to the anterior edge of the spine. Furthermore, the general shape of said first portion 10 is substantially semicircular so as to correspond to the shape of the vertebral plate. This optimizes the grafting area defined by the implant.

Figure 3:
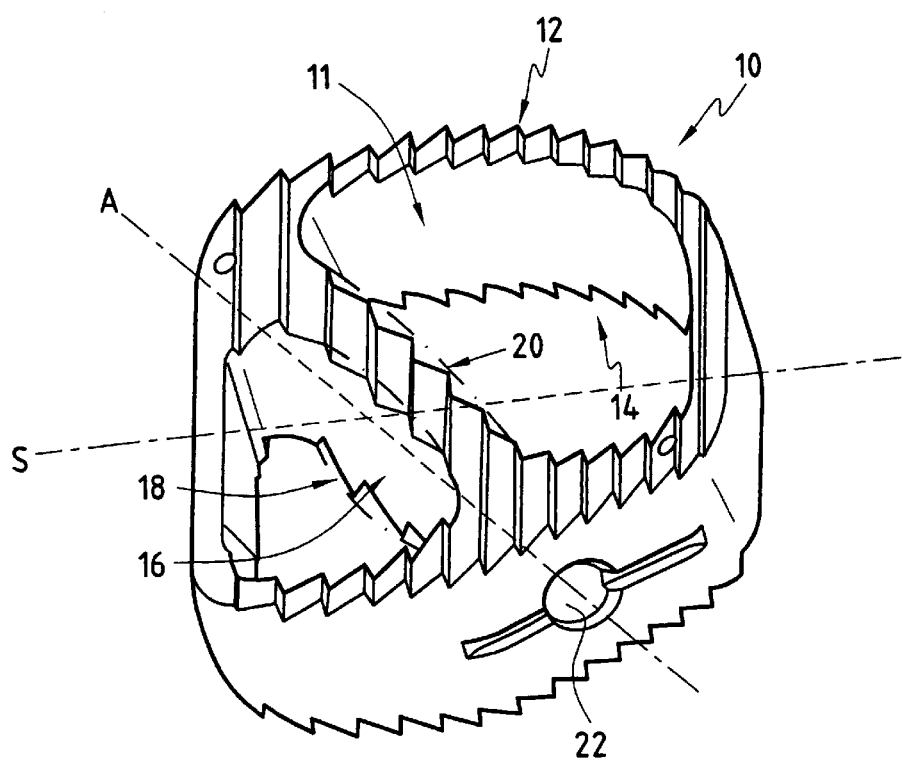
FIG. 3 is a diagrammatic perspective view showing another embodiment of an intersomatic implant.

In another particular embodiment of the invention, as shown in FIG. 3, the second portion 16 is oblique relative to the axis of symmetry S of the first portion 10. Similarly, the blind hole 22 passing through the side edge of the annular first portion 10 extends along said second portion 16 on its axis A which is oblique relative to the axis of symmetry S.

This configuration makes it possible to insert the implant along a direction that is oblique relative to the anterior edge of the spine, which can be necessary for certain intervertebral spaces that are difficult to access.

As shown in FIG. 3, the elongate second portion of axis A and the axis of symmetry S of the first portion form an angle substantially equal to 45°. Nevertheless, the second portion can be placed in such a manner as to form an angle lying in the range 0° to 90° relative to said axis of symmetry S.

In a preferred embodiment, the implant is made of a macromolecular material having elastic deformation properties close to those of bone, and more particularly lying between those of cortical bone and those of spongy bone.

For spongy bone, the modulus of elasticity or Young's modulus is about 0.1 gigapascals (GPa) while for cortical bone it is about 12 GPa. Consequently, the marcomolecular material is selected from synthetic materials having a modulus of elasticity lying in the range 0.1 GPa to 12 GPa.

The material preferably presents a modulus of elasticity lying in the range 1 GPa to 6 GPa so as to constitute a good compromise so that when it is inserted between two vertebrae, there is no discontinuity in the elastic mechanical properties of the assembly formed by the vertebrae and the implant.

Advantageously, the implant is molded as a single piece of polyether ether ketone. This material has a modulus of elasticity of 3.5 GPa.

It is economically advantageous to be able to mold the implant since that enables intersomatic cages to be produced at cost lower than the cost of producing cages out of titanium alloy.

In yet another particular embodiment, the open area of the implant corresponding to the sum of the areas defined by the intersection of a midplane of the implant with said two apertures, when divided by the total area defined by the intersection of the midplane with the outline of said first portion corresponds to a ratio lying in the range 0.75 to 0.95.

Figure 4:
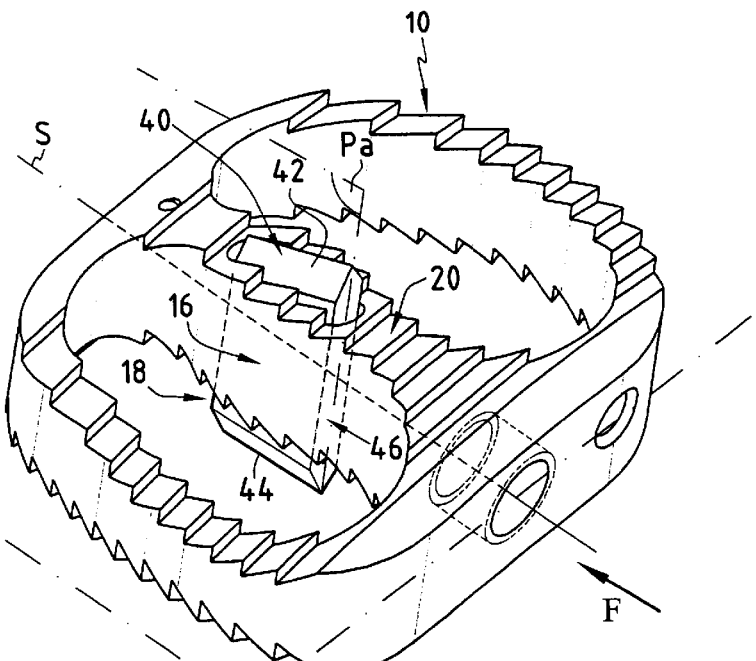
FIG. 4 is a diagrammatic perspective view showing yet another embodiment of an intersomatic implant.
Figure 5:
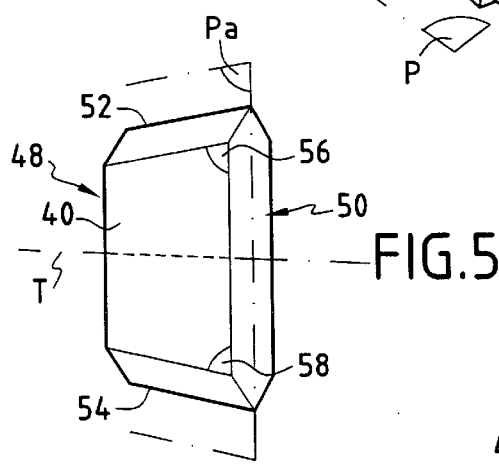
FIG. 5 is a diagrammatic perspective view showing a detail of the intersomatic implant shown in FIG. 4.

There follows a description of another particular embodiment of the invention with reference to FIGS. 3, 4, and 5, in which the implant is preferably inserted between cervical vertebrae.

FIG. 4 shows an implant comprising a first portion 10 and a second portion 16 interconnecting two opposite edges of the first portion 10. In a manner analogous to the second portion shown in FIG. 2, the second portion 16 has a bottom second edge 18 and a top second edge 20. In contrast, it is provided with an anchoring piece 40 which is preferably made of titanium alloy so as to be biocompatible and extremely strong. The anchoring piece 40 has a first end 42 which projects from the top second edge 20, and a second end 44 which projects from the bottom second edge 18.

For this purpose, the second portion 16 has a slot 46 that is generally in the form of a rectangular parallelepiped that opens out into the bottom second edge 18 and into the top second edge 20, and whose four edges formed between the inside walls of the slot 46 extend substantially perpendicularly to the midplane P of the first portion 10. As a result, the anchoring piece 40 which is of a size slightly greater than that of the slot 46 can be forced to pass right through the slot. It is thus held in a fixed position relative to the second portion 16 by friction between the inside walls of the slot 46 which are spread apart perceptibly from one another.

Naturally, the dimensions of the anchoring piece 40 between its two ends 42 and 44 are greater than the dimensions of the slot 46 so that both ends 42 and 44 project from respective second edges 18 and 20.

FIG. 5 shows the anchoring piece 40 in perspective. It is trapezoidal in shape presenting two opposite first edges 48 and 50 that are parallel to each other forming the bases of the trapezoid, and two opposite second edges 52 and 54 forming identical angles with the axis of symmetry T of the anchoring piece 40.

Thus the anchoring piece 40 has two identical acute angled corners 56 and 58 that are suitable for penetrating into the surfaces of the vertebral plates.

The anchoring piece 40 defines a midplane Pa and it is inserted in the slot 46, as shown in FIG. 4, so that the midplane Pa is perpendicular to the midplane P of the first portion 10. In addition, it is inserted in such a manner that the direction F along which the implant is inserted into the intervertebral space corresponds to a direction going from the longer first edge 50 towards the shorter opposite edge 48. It will be understood that this disposition prevents the anchoring piece from braking insertion of the implant into the intervertebral space with the ends 42 and 44 pressing against the vertebral plates of two vertebrae. It will also be understood that the two corners 56 and 58 of the anchoring piece which penetrate into the vertebral plates during insertion of the implant constitute significant locking means for the anchoring piece 40 and thus for the implant, in particular against movement in the direction opposite to the insertion direction. This ensures that the implant is held more effectively between the two vertebrae.

Figure 6:
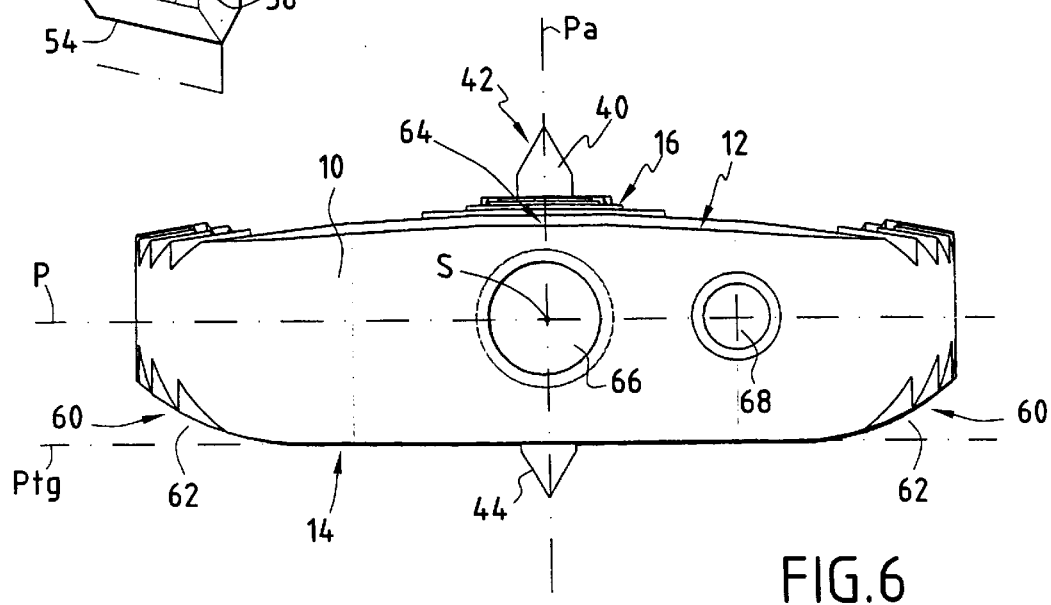
FIG. 6 is a diagrammatic front view of the intersomatic implant shown in FIG. 4.

FIG. 6 shows the implant in front view, provided with the anchoring piece 40 whose first end 42 appears above the first portion 10 and whose second end 44 appears below it.

In this particular embodiment, where the implant is generally inserted between two cervical vertebrae, the first portion 10 is not exactly symmetrical about its midplane P. As can be seen in FIG. 6, the bottom first edge 14 has curved regions 60 towards the sides of the first portion 10, leaving empty spaces 62 between the plane Ptg that is tangential to the first portion 10 and the bottom first edge 14. In addition, the top first edge of the first portion has a convex region 64 where the second portion 16 joins the first portion 10.

By means of this configuration, the intersomatic implant accurately matches the shape of the intervertebral space, particularly for cervical vertebrae.

Given this asymmetry, the implant must be inserted in a predetermined direction. To do this, a main blind hole 66 situated on the axis of symmetry S is suitable for receiving the tool and a steering hole 68 enables the implant to be steered in the predetermined direction.

Figure 7:
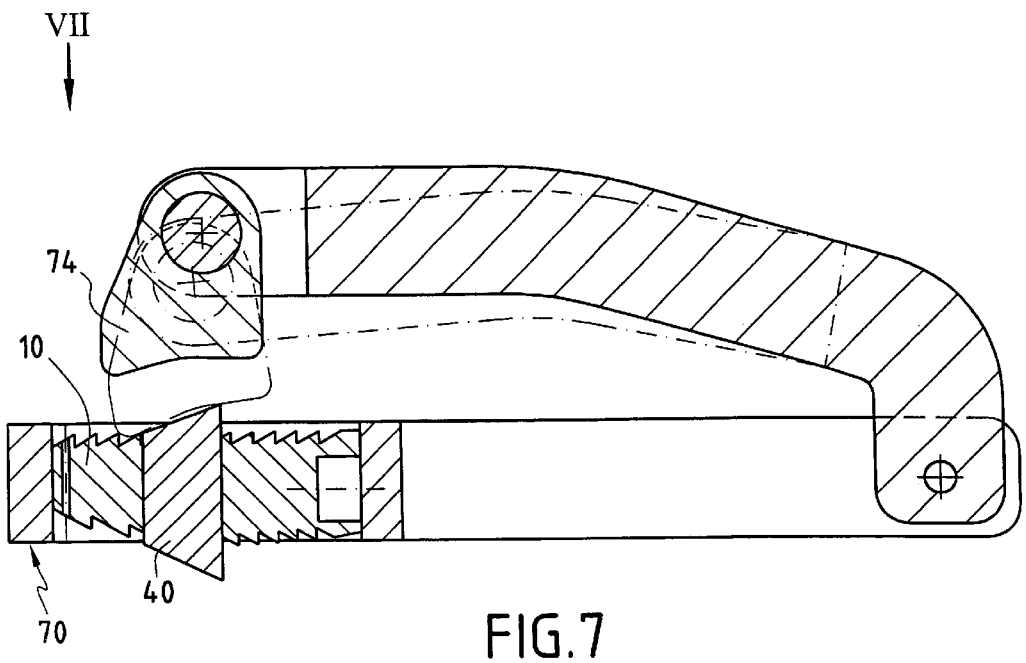
FIG. 7 is a diagrammatic section view through an intersomatic implant press.
Figure 8:
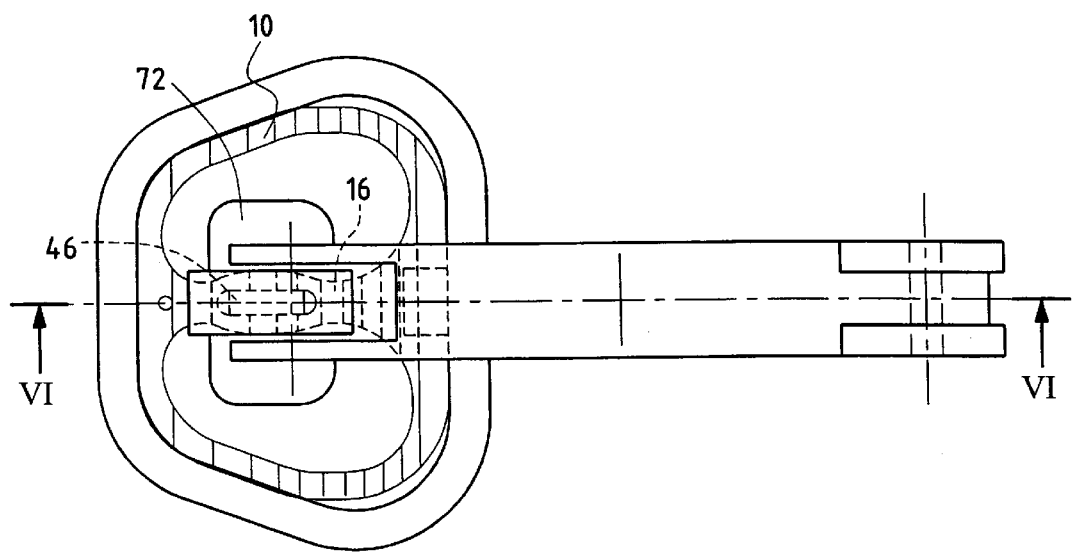
FIG. 8 is a diagrammatic plan view of the intersomatic implant press shown in FIG. 7.

The invention also provides an intersomatic implant press for inserting or removing said anchoring piece 40 in or from said slot 46. The press is described with reference to FIGS. 7 and 8.

The implant press has a first jaw 70 suitable for receiving the implant as constituted by the first portion 10 with the second portion 16 interconnecting two opposite edges, the anchoring piece 40 being inserted in said second portion 16. The first jaw 70 has a central aperture 72 shown in FIG. 8 suitable for allowing the anchoring piece 40 to pass through when it is forced through the slot 46 in the second portion 16. The press has a second jaw 74 for bearing against the anchoring piece 40 so as to insert it when the jaws 70 and 74 are moved towards each other. For this purpose, each jaw 70, 74 is extended by an arm, and the arms are connected together so as to pivot one relative to the other.

In addition, when the anchoring piece is preinstalled in the second portion 16 it is easily extracted by force using the press, should the operation require an implant to be inserted that is not fitted with an anchoring piece.

What is claimed is:

1. An intersomatic implant suitable for containing at least one bone graft and for being inserted in the intervertebral space along a predetermined direction, said implant comprising:

a first portion of generally annular shape surrounding an aperture and presenting a top first edge and a bottom first edge and an outer external surface; and a second portion of elongate shape along its main axis presenting a bottom second edge and a top second edge, and interconnecting two facing opposite regions of said first portion along said predetermined direction, thereby dividing said aperture into two housings suitable for containing said bone graft, at least one of said bottom and top second edges projecting from the space defined by said bottom and top first edges of the first portion, said first portion having a hole wherein the hole is a blind opening in said external surface of said first portion at a location corresponding to one of said interconnecting regions and extending along said main axis into said second portion.

2. An intersomatic implant according to claim 1, wherein said first portion and said second portion are connected together so as to form a single piece.

3. An intersomatic implant according to claim 1, wherein said bottom and top second edges of said second portion are curvilinear in shape with their ends running into said bottom and top first edges respectively of said first portion.

4. An intersomatic implant according to claim 1, wherein said bottom and top edges of said first and second portions present serrations suitable for constituting anchoring points in said vertebrae.

5. An intersomatic implant according to claim 1, wherein said first portion of generally annular shape has at least one axis of symmetry.

6. An intersomatic implant according to claim 5, wherein said second portion interconnects said two opposite regions of said portion along said axis of symmetry.

7. An intersomatic implant according to claim 5, wherein said second portion interconnects said two opposite regions of said first portion along a direction that is at an angle lying in the range from 0° to 90° with said axis of symmetry.

8. An intersomatic implant according to claim 5, wherein said first portion is generally substantially semicircular in shape.

9. An intersomatic implant according to claim 1, wherein said first portion and said second portion are molded as a single piece of macromolecular material.

10. An intersomatic implant according to claim 1, wherein said first portion and said second portion are made of polyether ether ketone.

11. An intersomatic implant according to claim 1, wherein said second portion further comprises anchoring means projecting from said top and bottom second edges, respectively.

12. An implant according to claim 1, wherein said two housings suitable for receiving a bone graft are substantially symmetrical with respect to said second portion.

13. An intersomatic implant, suitable for containing at least one bone graft and for being inserted in the intervertebral space along a predetermined direction, the implant comprising:

a first portion (10) of generally annular shape surrounding an aperture (11) and presenting a top first edge (12) and a bottom first edge (14); and a second portion (16) of elongate shape along its main axis (A) presenting a bottom second edge (18) and a top second edge (20), and interconnecting two facing opposite regions of said first portion (10) along said predetermined direction, thereby dividing said aperture (11) into two housings suitable for containing said bone graft, at least one of said bottom and top second edges projecting from the space defined by said bottom and top first edges (14, 12) of the first portion (10), wherein said second portion further comprises anchoring means projecting from said top and bottom second edges, respectively, and wherein said anchoring means comprises an anchoring piece having two ends, and wherein said second portion has a slot opening out into said bottom and top second edges so that said anchoring piece when inserted in said slot passes through said second portion, the first end projecting from said top second edge and the second end projecting from said bottom second edge of said second portion.

14. An intersomatic implant according to claim 13, wherein said anchoring piece is substantially trapezoidal in shape, its two ends being defined by the two non-consecutive and non-parallel sides thereof.

15. An intersomatic implant according to claim 14, wherein said anchoring piece presents a midplane, wherein said anchoring piece is inserted in said second portion so that said main axis A of said second portion intersects the two bases of the trapezoid, and its midplane is substantially perpendicular to the midplane of said first portion.

16. An intersomatic implant according to claim 14, wherein one of the bases of the trapezoid forms two acute angles with the two non-parallel sides, and wherein said anchoring piece is inserted in said second portion so that the insertion direction of said implant extends from the longer base towards the shorter base of the trapezoid.

17. An implant according to claim 13, wherein said anchoring piece is made of titanium alloy.

18. An intersomatic implant press for inserting said anchoring piece in said slot in accordance with claim 13, the press comprising:

a first jaw suitable for receiving said first portion in which said second portion interconnects two opposite edges, said first jaw having a central aperture in register with said slot in said second portion; and a second jaw placed facing said central slot;

wherein said first and second jaws are capable of being moved towards each other in such a manner that said second jaw can bear against said anchoring piece to force it into said slot or to extract it from said slot.

* * * * *